Dec. 19, 1939. H. A. VERSCHUREN Plant Pat. 350
ROSE
Filed April 18, 1939
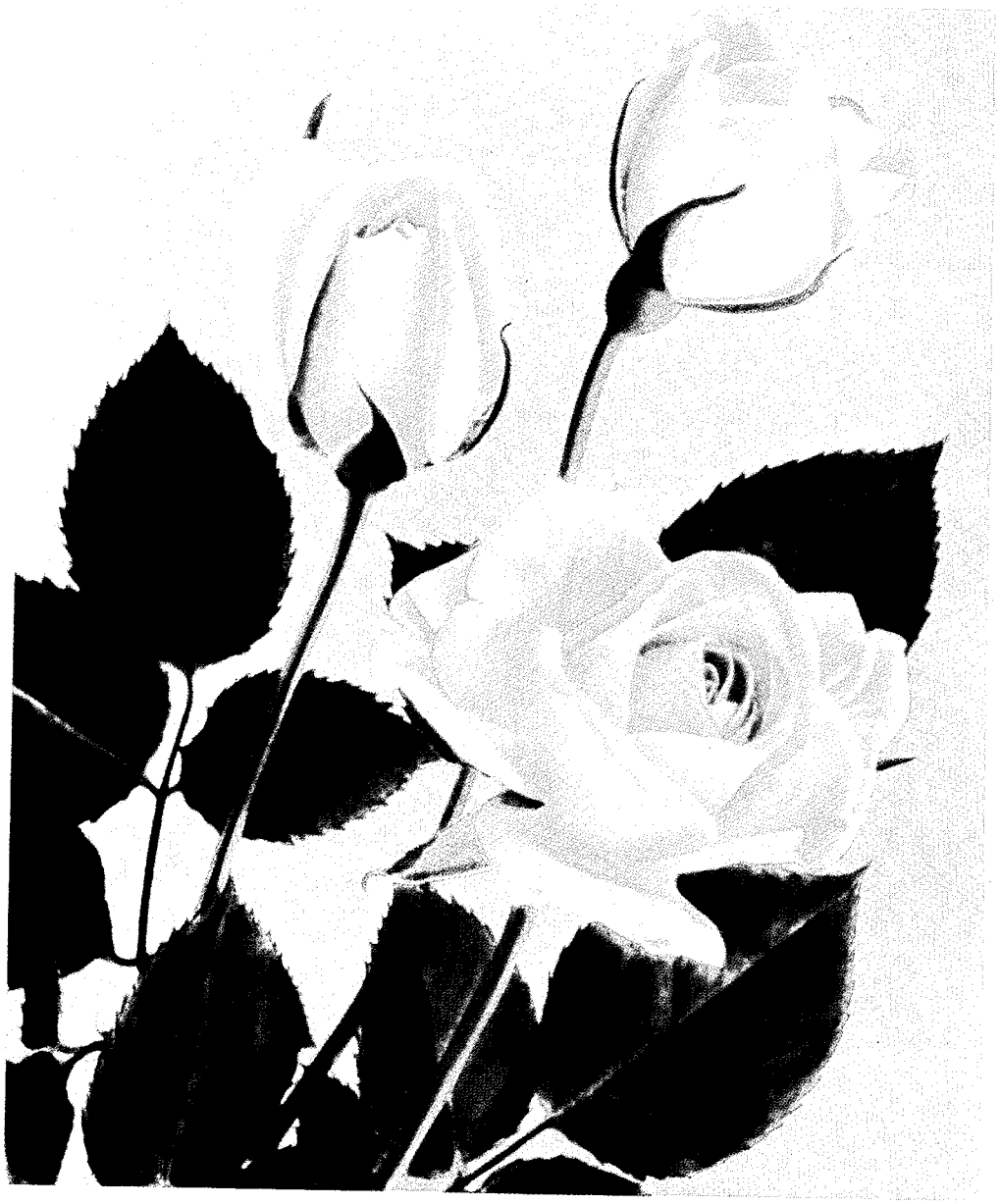
INVENTOR
Hendrikus Antonie Verschuren
By Orville M. Kile
Plant Patent Agent.

Patented Dec. 19, 1939

Plant Pat. 350

UNITED STATES PATENT OFFICE

350

ROSE

Hendrikus Antonie Verschuren, Haps, near Uden, Netherlands, assignor to Henry A. Dreer, Incorporated, Philadelphia, Pa., a corporation of New Jersey Application April 18, 1939, Serial No. 268,612

1 Claim. (Cl. 47—61)

My new invention is the result of definite breeding efforts in my gardens and is a cross between Mrs. Van Rossen and an unknown seedling. The most outstanding feature of this rose is its distinctive and brilliant coloring although its vigor and freedom of growth are also notable. Asexually reproduced plants have retained these marked characteristics.

The original paintings accompanying this application show three roses of this variety in various stages of opening, together with a portion of the stems and leaves, in approximately their true colors.

Following is a detailed description of my new variety of rose. Color plate references indicate Ridgway's Color Standards and Nomenclature. Where no plate numbers are given, ordinary dictionary terms are intended.

*The plant*

Growth:

Vigorous and upright bush, attaining a height of about 18 inches. Blooms and branches freely.

Stem:

Long; stout; have many thorns.

*Thorns*—Sharp-pointed; pink to red; large; downward-pointing.

*Nodes*—Shorter than usual for hybrid teas.

*Color*—Forest Green (Plate XVII), sometimes bronzed on side next sun.

Foliage:

Abundant; medium size; glossy.

*Leaves*—Compound, usually composed of 5 leaflets. Leaflets: shape—ovate with acuminate apex; size—terminal leaflet 2¼ to 2½ inches long by 1½ to 1¾ inches wide; color—upper surface Empire Green (Plate XXXII). Under surface Pois Green (Plate XLI). Edge usually has reddish tinge.

*Rachis*—Heavy; grooved and reddish-tinged above; sharp thorns below.

*Stipules*—Narrow; clinging; sharp-pointed.

*The flower*

Bud:

*Peduncle*—Long; sturdy; covered with fine prickles; Cress Green (Plate XXXI), frequently bronzed on side next sun.

*Size*—Large; averages 2½ inches long just before unfolding.

*Form*—Long-pointed.

*Color*—Entirely Empire Yellow (Plate IV) except for the vivid contrast formed by the visibility of a portion of the inner surface. The petals opening first usually curl backward horizontally permitting a stripe of the vivid inner surface to appear on the yellow bud. The inner surface of the outer petals of the opening bud is a color between Grenadine and Flame Scarlet (Plate II).

*Opening*—Opens slowly and perfectly.

*Sepals*—Broad and not foliaceous. Inner surface is covered with white fuzz. Sepals do not turn backward until after the bud has opened.

Blooms:

*Size*—Large, averaging 5 to 5½ inches across.

*Form*—High-centered at first; later opens cup-shaped with the outer petals quilled.

*Petalage*—Double, having in February about 35 petals.

*Petals*—Size—outer petals about 1¾ inches wide by 2¼ inches long. Shape—obovate. Substance—heavy and soft. Arrangement—regular. Color—the blossom is decidedly two-toned, the inner surface of the petals contrasting sharply with the outer surface. The outer surface is almost uniformly Empire Yellow (Plate IV). The color of the inner surface of the outer row of petals lies between Grenadine and Flame Scarlet (Plate II). The inner surface of the inner petals tends slightly more toward the pink and in the fully opened flower approaches a color which would fall between light Coral Red (Plate XIII) and Rose Doree (Plate I). Because of the distinctive color of this rose and the fact that the exact color is not found in Ridgway's Color Standards, it is difficult to indicate it accurately.

*Longevity*—Lasts well as a cut flower.

*Behavior*—Petals cling a long time then drop off cleanly.

*Fragrance*—Moderate.

*Reproductive organs*

Stamens:

Many; irregularly bunched around pistils.

*Filaments*—Irregular lengths, with some unusually long. Approximately Primuline Yellow (Plate XVI) with orange tinge at base.

*Anthers*—Medium size; color is light brown, approximately Ochraceous-Tawny (Plate XV).

Pistils:

Many; bunched.

*Styles*—Uneven; shorter than most of the surrounding stamens; white.

*Stigmas*—Light yellow.

Hips:

Large; blunt.

Having thus disclosed my invention, I claim:

A new and distinct variety of hybrid tea rose, characterized particularly by its free and vigorous growth, and its distinctive and brilliant two-toned blossoms having petals with their inner surface principally orange and their outer surface vivid yellow, substantially as shown and described.

HENDRIKUS ANTONIE VERSCHUREN.